(12) United States Patent
Pakstaite

(10) Patent No.: US 9,915,638 B2
(45) Date of Patent: Mar. 13, 2018

(54) BIO-REACTIVE FOOD EXPIRY LABEL

(71) Applicant: Solveiga Pakstaite, London (GB)

(72) Inventor: Solveiga Pakstaite, London (GB)

(73) Assignee: Mimica Lab Ltd, Herefordshire (GB)

( * ) Notice: Subject to any disclaimer, the term of this patent is extended or adjusted under 35 U.S.C. 154(b) by 0 days.

(21) Appl. No.: 15/310,779

(22) PCT Filed: May 20, 2015

(86) PCT No.: PCT/GB2015/051477
§ 371 (c)(1),
(2) Date: Nov. 13, 2016

(87) PCT Pub. No.: WO2015/185889
PCT Pub. Date: Dec. 10, 2015

(65) Prior Publication Data
US 2017/0082589 A1    Mar. 23, 2017

(30) Foreign Application Priority Data
Jun. 3, 2014  (GB) .................... 1409860.2

(51) Int. Cl.
*G01N 33/02*  (2006.01)
*G01N 33/00*  (2006.01)

(52) U.S. Cl.
CPC ......... *G01N 33/02* (2013.01); *G01N 33/0001* (2013.01)

(58) Field of Classification Search
USPC ........................................ 73/865.7
See application file for complete search history.

(56) References Cited

U.S. PATENT DOCUMENTS

| | | | |
|---|---|---|---|
| 2,823,131 A | 2/1958 | Power | |
| 3,786,777 A * | 1/1974 | Smith | G01K 11/06 116/206 |
| 5,876,741 A | 3/1999 | Ron | |
| 6,397,503 B1 * | 6/2002 | Cain | G09D 3/02 116/205 |
| 7,014,816 B2 * | 3/2006 | Miller | G01N 31/22 422/421 |
| 2004/0115319 A1 | 6/2004 | Morris et al. | |
| 2006/0057022 A1 | 3/2006 | Williams et al. | |
| 2010/0263244 A1 * | 10/2010 | Tabirian | G09F 3/0291 40/299.01 |

(Continued)

FOREIGN PATENT DOCUMENTS

FR    2938962    11/2008
JP    2002 142739    5/2002

(Continued)

*Primary Examiner* — Harshad R Patel
*Assistant Examiner* — Octavia Hollington
(74) *Attorney, Agent, or Firm* — Hartman Titus PLC; Joseph W Mott

(57) ABSTRACT

A food expiry label includes a layer of material (such as a water-swollen mammalian gelatine) that undergoes a phase transition (such as from solid to liquid) upon exposure to bacteria or fungi that result in food spoilage. The label may incorporate a tactile surface that the user can feel underneath the layer of gelatine once the gelatine has changed from solid to liquid. Thus a user can detect when a foodstuff is likely to have spoiled or been on the shelf for a predetermined period simply by feeling the label.

10 Claims, 2 Drawing Sheets

10

20

30

40

(56) References Cited

U.S. PATENT DOCUMENTS

2012/0107191 A1     5/2012   Strahle et al.
2012/0276647 A1    11/2012   Mills et al.
2016/0327538 A1*   11/2016   La Valle Sansone .. G01N 31/22

FOREIGN PATENT DOCUMENTS

JP         2013 220039     10/2013
WO     WO 00/23663      4/2000

* cited by examiner

10

20

30

40

BIO-REACTIVE FOOD EXPIRY LABEL

FIELD OF THE INVENTION

This invention relates to a bio-reactive expiry label for foodstuffs, for example protein-based foods.

BACKGROUND

Most packaged foods are sensitive to microbial attack, especially by bacteria and fungi. Both the colour and the flavour of foods can be adversely affected as well as the amount of microbes present render the food harmful to eat. To ensure freshness and safety, foodstuffs are labelled with an expiry date or 'best before' date. This is arrived at empirically or by modelling the material in a laboratory. Often a safety margin is included in this estimate such that food is often thrown away when it is perfectly safe to eat. Conversely, the wrapping maybe damaged or the packing is carried out under conditions of less than expected hygiene and the food becomes unsafe quicker than the expiry label suggests.

Most current expiry dates are static and do not react to environmental changes such as temperature or moisture, which act as catalysts for microbial growth on food. At the same time, printed expiry dates are inconspicuous and often cause large amounts of food to be wasted, quite often unnecessarily.

There is art that describes the use of coloured strips inside or intimately associated with the packing that detects the presence of gases associated with decaying food. Often these measure the pH of the gas inside the packing. Higher pH gases are associated with decay. Examples of this art are shown for instance in US patent application 20040115319, others by the same inventor and US applications 20040115319 and 20120107191. These colour changing materials may be incorporated into polymers as described in US application 20120276647.

FR 2938962 A1 (Viguie Jean Pierre) discloses a device for displaying whether a temperature threshold has been exceeded, comprising a container filled with a coloured liquid which is solidified under the action of a gel, and which is transformed into a liquid state if a predetermined temperature is reached or exceeded.

U.S. Pat. No. 2,823,131 (Power) discloses a food spoilage indicator comprising a reagent and a material which changes colour when contacted with the reagent, wherein contact of the two components is delayed by freezing the foodstuff and the indicator and can be further delayed by enclosing the colour change material in a water soluble material.

There is currently no simple way for a blind and partially sighted consumer to be able to check the expiry date of foodstuffs independently as this information is only exclusively provided visually at present. Difficulties may also be faced by people with learning difficulties, children and also people who have never learned to read.

SUMMARY OF INVENTION

In a first aspect of the present invention, there is provided a device for enabling the spoilage or age of a foodstuff to be detected, including a container containing a material that undergoes a phase transition resulting in a tactile change either over time or when it comes into contact with a substance which causes the foodstuff to spoil, whereby the tactile change indicates that the foodstuff has been spoiled or has reached a certain age.

The user can easily detect a change in the device (and by implication in the foodstuff) by feeling the tactile change in the material.

In a preferred embodiment, said material is a hydrocolloid gel. For example, the material could be one of the classes of hydrocolloid gel shown in Table 1 below:

TABLE 1

VARIATIONS OF HYDROCOLLOID GELS

| | | Protein | |
| --- | --- | --- | --- |
| Polysaccharides | Fish gelatine | Mammalian gelatine | Synthetic |
| Alginates | Cold water fish | Pig | |
| Biopolymers | Warm water fish | Cow | |
| Carrageenens | | Horse | |
| Galactomannans | | Etc. | |
| Pectins | | | |
| Starches | | | |

In a particularly preferred embodiment, the material is mammalian gelatine (e.g. water-swollen mammalian gelatine), agar-agar, carrageen, pectin, konjac, a vegetable gum-based gel, an insect gum-based gel, or a synthetic collagen. The concentration of the material is preferably between 1-10% (with the remainder being water)

A particularly preferred mammalian gelatine may be obtained from the following supplier: Jellice Pioneer Europe B.V., Kapitein Antiferstraat 31, 7821 BG Emmen, The Netherlands.

Preferably, said material changes from solid to liquid either over time or when it comes into contact with a substance which causes the foodstuff to spoil.

The device preferably includes a textured surface (e.g. a series of bumps or ridges), wherein said phase transition material forms a layer over at least a part of said surface, whereby said phase transition enables the user to detect said textured surface through said layer.

The layer of phase transition material may have an area from 25 mm$^2$ to 2500 mm$^2$, preferably about 400 mm$^2$. For example, said layer could be square with dimensions from 5×5 mm to 50×50 mm, optimally 20×20 mm.

The thickness of the layer may be from 1 mm to 10 mm, preferably from 2 mm to 3 mm.

In a preferred embodiment, there is provided a multi-layer label, containing a solid or gelled material that is rendered liquid by action of the food-spoiling bacteria or fungi, such as water swollen mammalian gelatine that is a solid gel when the label is manufactured, and then gradually breaks down into a liquid form so that a textured layer can be felt through the liquid. Mammalian gelatine is a protein, made by hydrolysing animal protein by a number of different methods as described for example in 'The Theory of the Photographic Process' 4$^{th}$ edition, Edited T. H. H. James, pp 55-56. It is this factor that allows it to be calibrated to model the decay rate of protein-based foods, such as meat. The bio-reactive food expiry label would preferably be adhered to a food package and in the same environment that the food is kept.

By using a calibrated natural substance to model the decay process of protein or pectin in the food material, the actual condition of the meat can be monitored by copying the same microbial and chemical changes because they would both be held in the same environment. The reactive nature of the label will allow for more accurate information about the condition of meat inside the package, rather than a static date that cannot update itself. This will either prevent food poisoning if the food expires before the printed date, or reduce food waste is the package has been stored correctly or even frozen, meaning that the meat can be consumed for a longer period of time than stated.

This invention will also give consumers the confidence that the food packaging had been kept in hygienic and safe conditions before it reached the retailer's shelf, thus enforcing greater brand loyalty and trust in the retail brand.

In a second aspect of the present invention, there is provided packaging for food or drink, incorporating a device as defined above. At least one wall of the container is formed from the same material as a material of the packaging.

In a further aspect of the present invention, there is provided an apparatus for detecting the spoilage of a food by using a label on the food packaging that contains a material (such as water-swollen mammalian gelatine) that changes from a solid or gel to a liquid when exposed to bacteria or fungi in a similar environment to the food storage container to reveal a tactile surface.

There may be a layer of gelatine that is a solid gel when the label is manufactured, and then gradually breaks down into a liquid form so that a textured layer can be felt through the liquid.

Preferably, there is a layer of a textured surface with a high enough relief to be easily detected by applying normal mechanical pressure and movement with human fingers.

The top and bottom plastic films may be made out of the same material as is used to cover the food package in order to maintain a similar environment.

The bottom plastic film is preferably adhered to a protein-based food package to allow for accurate tracking of the condition of the food contained inside.

INTRODUCTION TO DRAWINGS

A number of preferred embodiments of the invention will now be described by referring to the accompanying drawings, in which.

DETAILED DESCRIPTION

Figure 1:
FIG. 1 shows the four-layer structure of the label in an exploded view.
Figure 1:
Figure 1:
Figure 1:
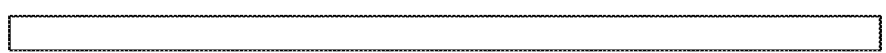

Turning to FIG. 1, mammalian gelatine gel layer 20 (obtained from Jellice Pioneer Europe B.V.) is placed on top of plastic textured sheet 30 and these are sandwiched between plastic film layers 10 and 40, using a plastic sealer. This four-layer label is then adhered to the protective film of a food package at the time when the food is being packed inside it, so that the microbial attacks are aligned with each other.

Figure 2:
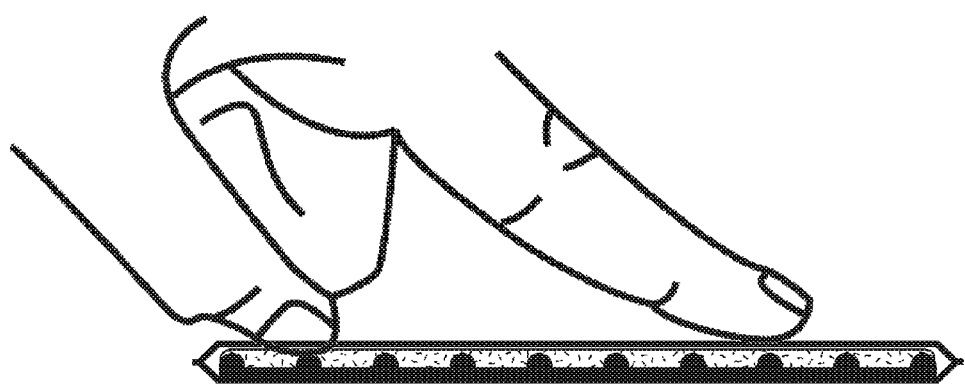
FIG. 2 shows an example of a fresh label with water-swollen gel.
Figure 3:
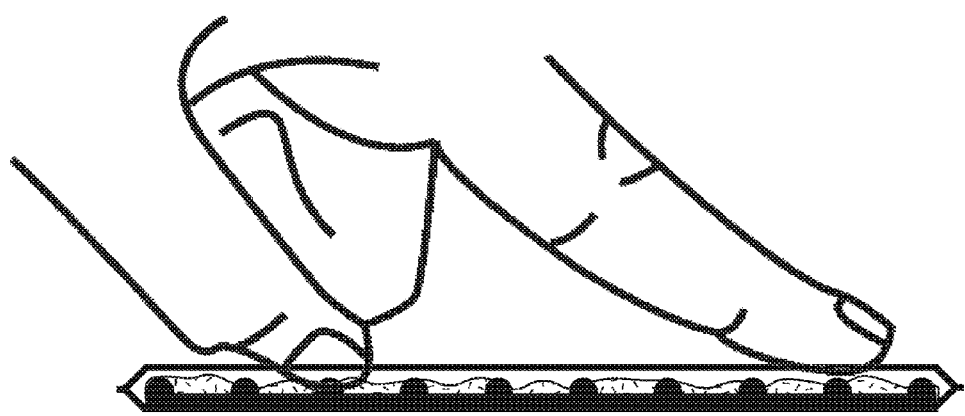
FIG. 3 shows an example of an old label and the change in the gelatine rigidity, which enables the textured sheet to be felt underneath.

If the label is checked by running a finger across the surface at this stage, the user would only feel a smooth, hard texture as the gelatine gel would still be in a solid state, as seen in FIG. 2, meaning that it is still fresh. The gelatine layer then proceeds to naturally decay at the same rate as the meat or fish, as seen in FIG. 3, and speeds or slows this process down according to warmer or cooler temperature changes, respectively. Once the food has been exposed to a warm enough environment for enough time for it to be no longer safe for consumption, the gelatine layer will also reflect this change by becoming a liquid, allowing the textured sheet 30 to be felt with the finger when the label is being checked.

Plastic film layer 10 will preferably have a printed semiotic graphic on it to enable the user to easily understand how to interact with the label.

The size of the label can vary, as long as it is a size large enough to be felt by human fingers. It is recommended that the assembled label area is no smaller than 4.5 cm squared. The sizes of each component need to be adjusted according to the desired size, with components 20 and 30 having to be the same size. Components 10 and 20 must be slightly larger.

Components 10 and 40 may be made out of the same material as the protective film on the food package on which the label is intended to be used. This is to create the most similar conditions to better model the decay process of the food. A very efficient combination for protecting food is a Polyamide/Polyethylene multilayer film, so this is the one that is usually used for packaging foods and so these components would also be likely to use this material.

Component 20 is water swollen mammalian gelatine to an approximate thickness of 3 mm. In order for the label to be most effective, the concentration of the gelatine is preferably between 1-10%. The gelatine is swollen and cut to size.

Component 30 can be made from any vacuum-formable plastic sheet with a suggested thickness of under 1 mm. A mould would first have to be made, with a suggested texture height of at least 2 mm. The plastic sheet can then be formed by heating and sucking it against the mould. The component is then cut down to size, which should match that of component 20.

Components 10 and 40 are then sealed together with heat, around components 20 and 30, as closely to their perimeters as possible. The label is then adhered to a food package.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in UK patent application number 1409860.2, from which this application claims priority, and in the abstract accompanying this application, are incorporated herein by reference.

The invention claimed is:

1. A device for indicating the spoilage of a foodstuff, comprising a container enclosing an indicating material that undergoes a phase transition resulting in a tactile change either over time or when it comes into contact with a substance which causes the foodstuff to spoil, and a component having a raised textured surface; the indicating material forming a layer over at least a part of the textured surface, whereby said phase transition enables the user to detect said textured surface through the indicating material, the tactile change indicating that the foodstuff has been spoiled.

2. A device as claimed in claim 1, wherein the indicating material is a hydrocolloid gel.

3. A device as claimed in claim 1, wherein the indicating material is mammalian gelatine, agar-agar, carrageen, pectin, konjac, a vegetable gum-based gel, an insect gum-based gel, or a synthetic collagen.

4. A device as claimed in claim 1, wherein said material is water-swollen mammalian gelatine.

5. A device as claimed in claim 1, wherein the indicating material changes from solid to liquid either over time or when it comes into contact with a substance which causes the foodstuff to spoil.

6. A device as claimed in claim 1, wherein the container has at least one wall which is formed from a porous material to enable ingress of said substance which causes the foodstuff to spoil.

7. A device as claimed in claim 1, additionally including means for attaching the device to a foodstuff or to the packaging of the foodstuff including an adhesive.

8. A device as claimed in claim 1, in the form of a food or drink label.

9. A method of detecting whether a foodstuff attached to or packaged with a device as in claim 1 has spoiled, comprising the steps of touching the device and feeling whether a phase transition indicating spoilage has occurred.

10. A method of detecting whether or not there has been spoilage of a foodstuff attached to or packaged with a device for indicating the spoilage of a foodstuff, comprising a container enclosing an indicating material that undergoes a phase transition resulting in a tactile change either over time or when it comes into contact with a substance which causes the foodstuff to spoil, and a component having a raised textured surface; the indicating material forming a layer over at least a part of the textured surface, whereby said phase transition enables the user to detect said textured surface through the indicating material, the method comprising the steps of touching the device and feeling whether a phase transition indicating spoilage has occurred.

* * * * *